United States Patent [19]

Mahjour et al.

[11] Patent Number: 4,908,389

[45] Date of Patent: Mar. 13, 1990

[54] PENETRATION ENHANCEMENT SYSTEM

[75] Inventors: Majid Mahjour, Morris Plains; Uma Iyer, Mendham; Mahdi B. Fawzi, Flanders, all of N.J.

[73] Assignee: Warner-Lambert Company, Morris Plains, N.J.

[21] Appl. No.: 900,865

[22] Filed: Aug. 27, 1986

[51] Int. Cl.⁴ ............ A61K 31/08; A61K 47/00
[52] U.S. Cl. .................... 514/772; 514/784; 514/788; 514/946; 514/947; 514/282
[58] Field of Search .......... 514/772, 784, 788, 946, 514/947, 282

[56] References Cited

U.S. PATENT DOCUMENTS 4,695,465  8/1988  Kigasawa et al. .......... 514/946

OTHER PUBLICATIONS

Chem. Abst. 105: 120803X, (1986), Stockebrand et al.
Martindale, The Extra Pharmacopoeia, 1982.
EPO Search Report–EPO 87 112 412.9.

*Primary Examiner*—Shep K. Rose
*Assistant Examiner*—Zohreh Fay
*Attorney, Agent, or Firm*—Ronald A. Daignault

[57] ABSTRACT

The penetration of various drugs through living membranes, eg., skin, is improved by their use in topical compositions containing certain penetration-enhancer systems.

2 Claims, No Drawings

PENETRATION ENHANCEMENT SYSTEM

BACKGROUND

The administration of drugs via oral routes is often associated with a variety of problems, eg., first pass metabolism, gastro-intestinal side effects, unpleasant taste and/or odor, and the like.

Recent studies have shown that the transdermal administration of drugs offers a viable alternative to oral dosage forms. However, transdermal delivery systems are not always efficacious due to such factors as the failure of the drug to sufficiently penetrate the cutaneous membrane and enter the body to produce therapeutic systemic effects.

The Invention

It has been discovered that various drugs can be effectively administered across a body membrane, eg., transdermally, using a novel combination of penetration enhancers.

These enhancers are generally thought of as solvents for the drug or drugs being used, but it is more accurate to term them penetration enhancers since—via a mechanism which is not clearly understood—they assist in the movement of an active ingredient across a living membrane, eg., the skin, and into the body fluid, eg., the blood stream. The systems which enhance transmembranal penetration are generally combinations of fatty acids and/or their esters.

The invention relates to compositions and methods for the administration of bioaffecting agents, eg., drugs, via living membranes, eg., skin, via topical application; ie., by contacting the compositions with the living membranes.

In a preferred embodiment, 0.5-3 wt. % procaterol is combined with 2-90 wt. % linoleic acid and 10-98% propylene glycol to produce compositions useful for transdermal administration.

Other aspects and advantages will be apparent from the following description of the invention.

Advantages

The compositions and methods of the invention have several advantages over the prior art delivery systems. Since the instant system permits delivery via buccal, rectal, mucosal, nasal and dermal membranes, the drug can enter the bloodstream without entering the gastro-intestinal tract. Transmembranal dosage forms generally do not produce the side effects, such as nausea and the like, which are often associated with the oral administration of drugs.

Furthermore, since the instant compositions need not be administered via injection, the unpleasantness of that type of delivery is avoided.

In general, it has been found that administration via penetration of the drug across a suitable membrane, eg., the cutaneous barrier, is superior to other routes of administration, especially in terms of ease of administration and attainment of sustained release.

Description of the Invention

Weight percentages are based on total composition weight unless stated otherwise.

Bioaffecting Agents

The bioaffecting agents which can be employed in the compositions of the invention include a wide range of known drug and beneficial substances and/or derivatives thereof.

By "derivatives thereof" is meant pharmaceutically acceptable derivatives of the bioaffecting base, or drug agent, as well as prodrugs and metabolites.

Using procaterol as an illustration, useful derivatives would include procaterol salts, with the hydrochloride salt being exemplary. Other useful forms of procaterol include procaterol base, procaterol sulfate and the like.

Mixtures of one or more such forms of a drug, as well as compositions containing a drug in combination with one or more other drugs, are contemplated.

Depending upon the bioaffecting agent(s) to be employed, a wide range of organic and inorganic salts thereof can be used. The nature of the salt is not essential as long as the drug or other agent maintains its value as a medicament and is compatible with the penetration enhancer(s) or other vehicle(s) employed. Exemplary acid salts include hydrochloride, hydrobromide, orthophosphate, benzoate, maleate, tartarate, succinate, citrate, salicylate, sulfate, acetate, and the like.

Useful bioaffecting agents include:

Antihistamines, such as chlorpheniramine maleate, phenindamine tartarate, pyrilamine maleate, doxylamine succinate, and pheyltoloxamine citrate;

Decongestants, such as phenylephrine hydrochloride, phenylpropanolamine hydrochloride, pseudoephedrine hydrochloride, ephedrine;

Various alkaloids, such as codeine phosphate, codeine sulfate and morphine;

Laxatives, vitamins and antacids;

Anticholesterolemic and antilipid agents;

Antiarrhythmics such as N-acetylprocainamide;

Antipyretics and analgesics such as acetaminophen, aspirin, and ibuprofen;

Appetite suppressants such as phenylpropanolamine hydrochloride or caffeine; and Expectorants such as guaifenesin.

Additional useful active medicaments include antiinflammatory substances, coronary dilators, cerebral dilators, vasodilators, anti-infectives, psychotropics, antimanics, stimulants, laxatives, decongestants, gastrointestinal sedatives, antidiarrheal preparations, antianginal drugs, vasodilators, antihypertensive drugs, vasoconstrictors and migraine treatments, antibiotics, tranquilizers, antipsychotics, antitumor drugs, anticoagulants and antithrombotic drugs, hypnotics, sedatives, antiemetics, antinauseants, anticonvulsants, neuromuscular drugs, hyper and hypoglycemic agents, thyroid and antithyroid preparations, diuretics, antispasmodics, uterine relaxants, mineral and nutritional additives, antiobesity drugs, anabolic drugs, erythropietic drugs, antiasthmatics, expectorants, cough suppressants, mucolytics, antiuricemic drugs, and the like. Mixtures may be used.

Preferred drugs for use in the instant compositions and methods are: procaterol, 4,5-dihydro-6-[4-(1H-imidazole-1-yl) phenyl]-5-methyl-3-(2H)-pyridazinone morphine, hydromorphone, propanolol, chlorpheniramine and derivatives thereof. Procaterol, the pyridazinone, propanolol and their derivatives are most preferred.

The daily dosages for human use of these preferred drugs are believed to be about 200 mg/day for procaterol and about 2 mg/day. for 45-dihydro-6-[4-(1H-imidazole-1-yl) phenyl]-5-methyl-3-(2H)-pyridazinone ("the pyridazinone") and higher for propanolol.

Penetration Enhancers

The penetration enhancer systems of the invention contain at least one fatty compound in combination with a non-fatty hydroxyl compound.

By "fatty" compounds applicants mean compounds related to, or existing as, any of the saturated or unsaturated monocarboxylic acids that occur naturally in the form of glycerides in fats and fatty oils.

The fatty compounds which can be employed are essential fatty acids, their esters, alcohols and other related compounds. Useful fatty components of the instant enhancement systems include saturated and unsaturated aliphatic compounds. Generally the unsaturated compounds contain about 8 to 24 carbon atoms.

Fatty acids, alcohols and esters to be employed herein include those containing oleic, linoleic, linoleic, moieties and the like. Mixtures are comtemplated.

The preferred group of fatty components include linoleic acid (ie., 9,12- octadienoic acid) and related compounds. Suitable esters of this or other fatty acid(s) to be employed include the $C_{1-3}$ esters eg., the methyl, ethyl, and propyl esters, and the like.

When an alcoholic fatty component is employed, it is generally preferred that it contain no more than one hydroxyl group, ie., monohydroxy alcoholic fatty compounds are preferred. One such compound is linoleyl alcohol.

The use of linoleic acid to enhance the penetration of anti-inflammatory and analgesic agents has been described in Kokai Tokyo Kobo, "Topical Anti-inflammatory and Analgesic Agent" Taisho Pharmaceutics Co., Ltd., Japan, 81, 110, 614 (cl. A61K31/135) Sept. 1, 1981.

In addition, several studies have been made on the function of linoleic acid, an essential fatty acid, in skin. Two of these are: C. Prottey, "Investigation of Functions of Essential Fatty Acids in the Skin," *British Journal of Dermatology* (1977), 97, 29; and E. O. Butcher, "The Penetration of Fat and Fatty Acid into the Skin of the Rat," *J. Investig. Dermatol.*, 1953, 43–48.

The mechanism by which the linoleic acid or its esters enhances the penetration of the instant combinations is not clearly understood. However, the changes brought about using the instant compositions are systemic and not merely local, ie., at the site where the composition is applied.

The other, or secondary, component of the penetrant system of the invention is not a fatty substance. Generally, this other component is a solvent for the bioaffecting agent. Useful solvents are generally monoor polyhydroxyl-containing compounds which may, optionally, contain ester groups.

Hydroxyl compounds to be used as the secondary component include compounds containing one or more hydroxyl groups. Polyols are preferred. Polyols containing one to four carbon atoms are more preferred. Propylene glycol, polyethylene glycols (eg., PEG 400) and tetraglycols are highly preferred. Isopropanol is also useful. Mixtures are operable.

The ester group-containing compound useful in the secondary component of the penetration enhancer system will be at least one compound which contains one or more ester groups. Compounds containing 6 to 30 carbon atoms and three or more ester groups are preferred. Saturated compounds containing about three to about five carbon atoms are more preferred. Triacetin and triethyl citrate are highly preferred. Mixtures are contemplated.

The penetration enhancer systems of the invention contain the primary or fatty component in combination with one or more of the secondary, or non-fatty, components.

Preferred enhancement systems will be composed of a fatty acid or ester, eg., linoleic acid, in combination with a glycol, eg., propylene glycol, and, optionally, an ester, eg., triacetin.

When more than one secondary component is used, the quantities thereof may vary as long as the total quantity of resulting penetrant is beneficial to penetration.

The Composition

The compositions which exhibit effective bioavailable ability when applied transmembranally include the bioaffecting and penetration enhancement portions in the following ranges.

TABLE 1

| | Weight Percentage Range | | |
|---|---|---|---|
| | Broad | Preferred | Highly Preferred |
| Bioaffecting agent (eg., drug) | 0.1–10 | 0.2–5 | 2 |
| Penetration System Fatty Component | 1–99 | 1–20 | 10 |
| Secondary Component | 0–99 | 80–99 | 90 |

The following examples illustrate the effectiveness of the penetration enhancers of the invention.

EXAMPLES

The experimental method employed to generate the data in the following examples was:

Skin sections from male hairless mice (5–7 weeks old) were mounted on Franz ® diffusion cells with the stratum corneum facing the donor compartment. To remove extraneous debris, the dermal side of the skin was in contact with saline for 2 hours before starting the diffusion experiment. One milliliter of a Procaterol solution was placed in the donor compartment which was then occluded with cellophane and Parafilm ®. The appearance of Procaterol in the receiver solution (saline) was monitored by withdrawing the entire contents of the receiver chamber at timed intervals. The receiver compartment was then refilled with fresh saline. The samples were filtered through a 0.45 u nylon filter and the drug concentration determined by HPLC. Temperature was maintained at 37° C. during the experiment.

Procaterol with Linoleic Acid (LA) and Propylene Glycol (PG)

The permeation of procaterol base through hairless mouse skin was significantly enhanced when a penetration system containing propylene glycol was used.

TABLE 2

Effect of Linoleic Acid Concentration in Propylene Glycol on the Permeation of Procaterol Base

| Vehicle LA:PG | Drug Conc. ug/mL | Flux ug/cm$^2$/h | P cm/sec $\times$ 10$^6$ | Lag Time (h) |
|---|---|---|---|---|
| 0:100 | 19.1 | 0.45 | 0.007 | — |
| 2:98 | 23.5 | 83.9 | 0.99 | 2.7 |
| 5:95 | 21.7 | 125.7 | 1.6 | 1.8 |
| 10:90 | 20.71 | 149.7 | 2.0 | 1.5 |
| 20:80 | 15.9 | 137.6 | 2.4 | 1.1 |
| 50:50 | 21.7 | 159.3 | 2.04 | 1.2 |
| 90:10 | 17.05 | 123.4 | 2.0 | 1.99 |

EXAMPLE 2

Procaterol with Linoleic Acid, Triethyl Citrate and Propylene Glycol

Solvent systems containing LA, PG and triethyl citrate (TEC) appear to be highly effective. The flux of procaterol base (PB) from four different formulations (F1 to F4) containing linoleic acid, triethyl citrate, and propylene glycol through hairless mouse skin is shown in Table 4.

TABLE 4

Permeation of Procaterol from the Formulations Containing Triethyl Citrate

| Formulation | Vehicle LA:TEC:PG | Drug Conc. mg/mL | Flux uG/cm$^2$/h | P cm/sec × 10$^7$ | Lag Time (h) |
|---|---|---|---|---|---|
| F1 | 10:80:10 | 16.9 | 32.0 | 5.26 | 14.7 |
| F2 | 10:70:20 | 23.03 | 33.5 | 4.04 | 14.7 |
| F3 | 20:60:20 | 19.35 | 46.0 | 6.60 | 4.9 |
| F4 | 20:50:30 | 44.7 | 65.8 | 4.10 | 7.3 |
| F5 | 20:50:30 | 4.32 (HCl salt) | 8.5 | 5.47 | 11.2 |

The loading capacity of F1 is less than 2%; whereas for F2 to F4 it is more than 2% of PB. The solvent system F5 was saturated with procaterol HCl and the flux of procaterol from this formulation was also measured. The loading capacity of F5 is about 0.5 percent procaterol HCl.

Table 5 shows the total amount of drug that permeated through 10 cm$^2$ of hairless mouse skin in the first 24 hours of the experiment and the calculated daily flux values (flux mg/cm$^2$/h 10 cm$^2$ 24 h). The observed differences between actual and calculated values are due to the lag time.

TABLE 5

Total Amount of Procaterol (mg) Delivered in First 24 Hours of Experiment

| Formulation | Calculated (m) | Actual (mg) |
|---|---|---|
| F1 | 7.68 | 1.75 |
| F2 | 8.04 | 2.9 |
| F3 | 11.04 | 9.1 |
| F4 | 15.79 | 10.94 |
| F5 | 2.04 | 1.1 |

EXAMPLE 3

Linoleic Acid and Propylene Glycol with 4,5-dihydro-6-[4-(IH-imidazole-1-wl) phenyl]-5-methyl-3-(2H)-pyridazinone.

In this example, the concentration of linoleic acid, a representative fatty acid, in propylene glycol was optimized to achieve a maximum permeability coefficient for the cardiotonic compound 4,5-dihydro-6-[4-(IH-imidazole-1-yl) phenyl]-5-methyl-3-(2H)-pyridazinone.

The base was prepared as follows: One gram of the hydrochloride of the pyridazinone was dissolved in 10 ml of water to which 3 ml of ammonium hydroxide was added. The precipitate (base) thus formed was extracted with chloroform (2 × 15 ml). The chloroform solution was washed with water and dried over anhydrous sodium sulfate. After evaporating the solvent, the pyridazinone base was obtained as a solid powder.

The addition of linoleic acid to propylene glycol was found to significantly enhance the permeation of the drug through the skin. A maximum flux was obtained at a linoleic acid concentration of 10%. Table 6 shows the permeability data for the drug, expressed in terms of the hydrochloride salt.

TABLE 6

Effect of Linoleic Acid Concentration in Propylene Glycol on the Permeation of Pyridazinone Base (expressed as Cl Salt)

| % Linoleic Acid | Concentration | Flux (ug/cm$^2$) | Permeability Coefficient (P) (cm/sec × 10$^7$) | P $P_x$* | Lag Time (h) |
|---|---|---|---|---|---|
| 0 | 26.38 | 0.4 | 0.042 | 1 | 6.2 |
| 10 | 43 | 492 | 31.8 | 755 | 1.75 |
| 40 | 43 | 337.3 | 21.8 | 517 | 1.45 |
| 80 | 43 | 148.5 | 9.6 | 227 | 1.29 |
| 100 | 31.5 | 24.5 | 2.2 | 51 | 5.35 |

*$P_x$ = Permeability coefficient of the drug from propylene glycol solution.

EXAMPLE 4

The results of replacing propylene glycol in the formulations of Example 3 with PEG 400 or with tetraglycol are shown in Table 7.

TABLE 7

Effect of Linoleic Acid on Permeation of Drug of Example 3 in Vehicles Containing PEG 40D or Tetraglycol

| Vehicle | Concentration | Flux (ug/cm$^2$/h) | Permeability Coefficient (P) (cm/sec × 10$^7$) | P $P_x$* | Lag Time (h) |
|---|---|---|---|---|---|
| Linoleic acid: PEG 400 20:80 | 41.7 | 114.3 | 7.6 | 181 | 3.5 |
| Linoleic acid: tetraglycol 20:80 | 20.09 | 186.69 | 25.8 | 614 | 5.58 |

*Permeability coefficient of the drug from propylene glycol solution

EXAMPLE 5

Propranolol with Linoleic Acid and Propylene Glycol

TABLE 8

Effect of Linoleic Acid Concentration in Propylene Glycol on the Permeation of Propranolol through Hairless Mouse skin

| Vehicle PG:LA | Drug Conc. (mg/ml) | Flux (ug/cm$^2$/h) | P (cm/sec × 10$^7$) | Lag Time (h) |
|---|---|---|---|---|
| 100:0 | 42 | 15.5 | 1.03 | 3.15 |
| 98:2 | 38 | 94.3 | 6.9 | 3.6 |
| 94:6 | 52 | 60.4 | 4.4 | 2.8 |
| 90:10 | 22 | 17.6 | 2.2 | 1.26 |
| 60:40 | 48 | 6.2 | 0.36 | 1.6 |
| 20:80 | 57 | 4.1 | 0.20 | 4.6 |

The maximum permeability coefficient was achieved when the linoleic acid concentration was less than 6%. Table 9 shows the effect of replacing propylene glycol in the formulation with other solvents.

TABLE 9

Effect of Concentration of Linoleic Acid in Various Solvents on the Permeation of Propranolol

| Vehicle | Drug Conc. (mg/ml) | Flux (ug/cm$^2$/h) | P (cm/sec × 10$^7$) | Lag Time (h) |
|---|---|---|---|---|
| IP:LA | | | | |
| 98:2 | 77 | 88.5 | 3.2 | 4.4 |
| 94:6 | 82 | 76.6 | 2.7 | 3.2 |
| IPM:LA | | | | |
| 60:40 | 50 | 4.6 | 0.25 | 1.98 |

TABLE 9-continued

Effect of Concentration of Linoleic Acid in Various Solvents on the Permeation of Propranolol

| Vehicle | Drug Conc. (mg/ml) | Flux (ug/cm²/h) | P (cm/sec × 10⁷) | Lag Time (h) |
|---|---|---|---|---|
| PEG 400:LA 20:80 | 51 | 3.76 | 0.2 | 4.6 |

Legend
IP = isopropyl alcohol
LA = linoleic acid
IPM = isopropyl myristate
PG = propylene glycol
PEG = polyethylene glycol The use of excipients and other conventional additives in the components and methods of the invention are contemplated.

Reasonable variations, such as those which would occur to a skilled artisan, can be made herein without departing from the scope of the invention.

We claim:

1. A transmembranally administrable composition comprising:
    (a) about 0.2% to about 5% of a bioaffecting agent selected from the group consisting of procaterol, 4,5-dihydro-6-[4-(1H-imidazole-1-yl)phenyl]-5-methyl-3-(2H)-pyridazinone, morphine, hydromorphone, propanolol, chlorpheniramine and a pharmaceutically acceptable organic or inorganic acid,
    (b) about 1% to about 202% of a fatty component selected from the group consisting of linoleic acid, $C_1$–$C_3$ linoleic esters, and a monohydroxy linoleyl alcohol,
    (c) about 80% to about 99% of a secondary component consisting of a mixture of a compound selected from the group consisting of isopropanol, propylene glycol, polyethylene glycol 400 and tetraglycol, and a compound selected from the group consisting of triacetin and triethyl citrate.

2. A method of administering a bioaffecting agent comprising contacting a transmembranally administrable composition comprising:
    (a) about 0.2% to about 5% of a bioaffecting agent selected from the group consisting of procaterol, 4,5-dihydro-6-[4-(1H-imidazole-1-yl)phenyl]-5-methyl-3-(2H)-pyridazinone, morphine, hydromorphone, propanolol, chlorpheniramine and a pharmaceutically acceptable organic or inorganic acid,
    (b) about 1% to about 20% of a fatty component selected from the group consisting of linoleic acid, $C_1$–$C_3$ linoleic esters, and a monohydroxy linoleyl alcohol,
    (c) about 80% to about 99% of a secondary component consisting of a mixture of a compound selected from the group consisting of isopropanol, propylene glycol, polyethylene glycol 400 and tetraglycol, and a compound selected from the group consisting of triacetin and triethyl citrate with a living membrane.

* * * * *